(12) United States Patent
Podilchuk et al.

(10) Patent No.: US 11,043,297 B2
(45) Date of Patent: Jun. 22, 2021

(54) NEURAL NETWORK-BASED OBJECT DETECTION IN VISUAL INPUT

(71) Applicant: Rutgers, The State University of New Jersey, New Brunswick, NJ (US)

(72) Inventors: Christine I. Podilchuk, Warren, NJ (US); Richard Mammone, Warren, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 16/989,625

(22) Filed: Aug. 10, 2020

(65) Prior Publication Data

US 2021/0050095 A1    Feb. 18, 2021

Related U.S. Application Data

(63) Continuation of application No. 16/218,832, filed on Dec. 13, 2018, now abandoned.

(51) Int. Cl.
| | |
|---|---|
| *G06K 9/00* | (2006.01) |
| *G16H 30/40* | (2018.01) |
| *A61B 5/00* | (2006.01) |
| *A61B 8/08* | (2006.01) |
| *G06T 7/00* | (2017.01) |

(Continued)

(52) U.S. Cl.
CPC .......... *G16H 30/40* (2018.01); *A61B 5/7267* (2013.01); *A61B 8/5223* (2013.01); *G06K 9/3233* (2013.01); *G06N 3/08* (2013.01); *G06T 7/0012* (2013.01); *G16H 30/20* (2018.01); *G16H 50/20* (2018.01); *G06T 2207/20081* (2013.01); *G06T 2207/20084* (2013.01)

(58) Field of Classification Search
None
See application file for complete search history.

(56) References Cited

U.S. PATENT DOCUMENTS

| 8,467,607 B1 | 6/2013 | Toshev et al. |
| 2012/0232390 A1 | 9/2012 | Park |

(Continued)

OTHER PUBLICATIONS

Redmon et al., "You Only Look Once: Unified, Real-Time Object Detection", May 9, 2016, 10 pages.

(Continued)

*Primary Examiner* — Wei Wen Yang
(74) *Attorney, Agent, or Firm* — Greenberg Traurig, LLP

(57) ABSTRACT

A device to detect an object in a medical image is described. An image analysis application, executed by the device, receives the medical image as an input. The medical image is next partitioned to sub-regions. Parts of the object are detected in a selection of the sub-regions using a deep-learning neural network (DNN) model. Bounding boxes for the selection are also determined. The bounding boxes are evaluated based on a confidence score detected as above a threshold level. The confidence score designates the parts as contained within the selection. Next, a region of interest (ROI) is determined as a group including the selection. Similar orientations associated with the bounding boxes are comparable to similar orientations of a positive training model of the DNN model. Furthermore, the selection is designated as the ROI within the medical image. The medical image is provided with the ROI to a user.

20 Claims, 5 Drawing Sheets

(51) Int. Cl.
  *G16H 30/20* (2018.01)
  *G16H 50/20* (2018.01)
  *G06K 9/32* (2006.01)
  *G06N 3/08* (2006.01)

(56) References Cited

U.S. PATENT DOCUMENTS

| | | |
|---|---|---|
| 2018/0293664 A1 | 10/2018 | Zhang et al. |
| 2018/0315188 A1 | 11/2018 | Tegzes et al. |
| 2019/0064841 A1 | 2/2019 | Tong et al. |
| 2019/0133693 A1* | 5/2019 | Mahfouz .................. A61B 6/12 |
| 2020/0054306 A1* | 2/2020 | Mehanian .............. A61B 8/486 |

OTHER PUBLICATIONS

Liu et al., "SSD: Single Shot MultiBox Detector", Dec. 29, 2016, 17 pages.

Ren et al., "Faster R-CNN: Towards Real-Time Object Detection with Region Proposal Networks", Jan. 6, 2016, 14 pages.

\* cited by examiner

NEURAL NETWORK-BASED OBJECT DETECTION IN VISUAL INPUT

CROSS-REFERENCE TO RELATED APPLICATION

This application is a continuation application, which relates to and claims the benefit to U.S. application Ser. No. 16/218,832, filed on Dec. 13, 2018, entitled "Object Detection in Medical Image", the entirety of which is incorporated herein by reference.

FIELD OF THE EMBODIMENTS

The field of the embodiments relate to a device to an object within a medical image. The object may be identified and labelled as a region of interest which contains a lesion (malignant).

BACKGROUND OF THE EMBODIMENTS

Information exchanges have changed processes associated with work and personal environments. Automation and improvements in processes have expanded the scope of capabilities offered for personal and business data consumption. With the development of faster and smaller electronics, a variety of devices have integrated into daily lives. A modern device includes components to provide variety of services such as communication, display, imaging, voice, and/or data capture, among others. Abilities of the modern device jump exponentially when networked to other resources that provide previously unimagined number of services associated with medical imaging.

Ultrasound and other medical imaging devices scan biological structures or tissues of a patient to provide images. The scanned images are provided to medical practitioner(s) to aid with diagnosis of illnesses such as cancer. Clarity and quality of scanned image are usually suspect and depend on variety of conditions associated with the patient and a skill of a technician capturing the scanned image. Furthermore, the medical practitioner is also subject to missed diagnosis or false diagnosis associated with the scanned image due to quality of the scanned image and/or human error.

SUMMARY OF THE EMBODIMENTS

The present invention and its embodiments relate to a method to detect an object in a medical image. In an example scenario, the method may include receiving the medical image as an input. The medical image may next be partitioned to sub-regions. Parts of the object may be detected in a selection of the sub-regions using a deep-learning neural network (DNN) model. Bounding boxes for the selection may also be determined. The bounding boxes may be evaluated based on a confidence score detected as above a threshold level. The confidence score may designate the parts as contained within the selection. Next, a region of interest (ROI) may be determined as a group including the selection. Similar orientations associated with the bounding boxes may be comparable to similar orientations of a positive training model of the DNN model. Furthermore, the selection may be designated as the ROI within the medical image. The medical image may also be provided with the ROI to a user.

In another embodiment of the present invention, a device to detect an object in a medical image is described. The device may be configured to receive the medical image as an input. The medical image may next be partitioned to sub-regions. Parts of the object may be detected in a selection of the sub-regions using a deep-learning neural network (DNN) model. Bounding boxes for the selection may also be determined. The bounding boxes may be evaluated based on a confidence score detected as above a threshold level. The confidence score may designate the parts as contained within the selection. Next, a region of interest (ROI) may be determined as a group including the selection. Similar orientations associated with the bounding boxes may be comparable to similar orientations of a positive training model of the DNN model. Furthermore, the selection may be designated as the ROI within the medical image. The selection within the ROI may be labelled with annotation(s) associated with a type of tissue. The type of tissue may include lobulated, spiculated, angular, clear boundary, oval, circumscribed, or abrupt interface. The medical image may also be provided with the annotation(s) and the ROI to a user.

In yet another embodiment of the present invention, a device to detection an objection in a medical image is described. The device may include a memory configured to store instructions associated with an image analysis application. A processor may be coupled to the memory. The processor may execute the instructions associated with the image analysis application. The image analysis application may include a computer assisted detection (CADe) module. The CADe module may be configured to receive the medical image as an input. The medical image may next partitioned to sub-regions. Parts of the object may be detected in a selection of the sub-regions using a deep-learning neural network (DNN) model. Bounding boxes for the selection may also be determined. The bounding boxes may be evaluated based on a confidence score detected as above a threshold level. The confidence score may designate the parts as contained within the selection. Next, a region of interest (ROI) may be determined as a group including the selection. Similar orientations associated with the bounding boxes may be comparable to similar orientations of a positive training model of the DNN model. Furthermore, the selection may be designated as the ROI within the medical image. The selection within the ROI may be labelled with annotation(s) associated with a type of tissue. The type of tissue may include lobulated, spiculated, angular, clear boundary, oval, circumscribed, or abrupt interface. The medical image may also be provided with the annotation(s) and the ROI to a user.

It is an object of the embodiments of the present invention to detect an object in a medical image.

It is an object of the embodiments of the present invention to partition the medical image to sub-regions.

It is an object of the embodiments of the present invention to determine a selection of the sub-regions associated with the object.

It is an object of the embodiments of the present invention to process the selection to determine a region of interest (ROI).

It is an object of the embodiments of the present invention to label the selection with annotation(s).

It is an object of the embodiments to provide the medical image, the annotation(s) and the ROI to a user.

These and other features, aspects and advantages of the present invention will become better understood with reference to the following drawings, description and claims.

DESCRIPTION OF THE PREFERRED EMBODIMENTS

Figure 1:
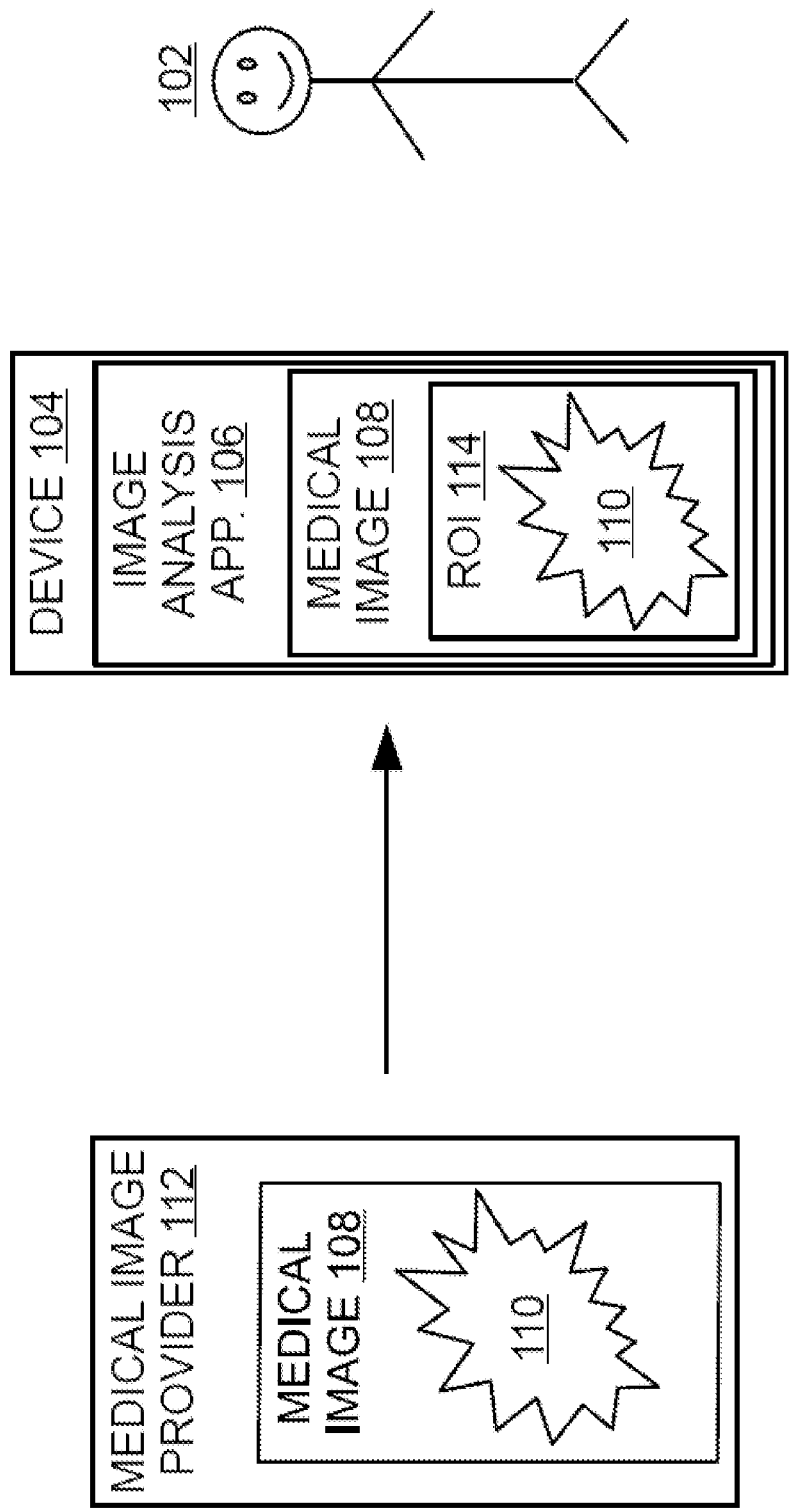
FIG. 1 shows a conceptual diagram illustrating examples of detecting an object in a medical image, according to an embodiment of the invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations may be made thereto.

FIG. 1 shows a conceptual diagram illustrating examples of detecting an object in a medical image 108. In an example scenario, a device 104 may execute (or provide) an image analysis application 106. The device 104 may include a physical computing device hosting and/or providing features associated with a client application (such as the image analysis application 106). The device 104 may include and/or is part of a smart phone, a tablet based device, a laptop computer, a desktop computer, a physical server, and/or a cluster of servers, among others. The device 104 may also be a node of a network. The network may also include other nodes such as a medical image provider 112, among others. The network may connect nodes with wired and wireless infrastructure.

The device 104 may execute the image analysis application 106. In an example scenario, the image analysis application 106 may receive the medical image 108 as an input. An example of the medical image 108 may include an ultrasound image (or scan). Other examples of the medical image 108 may include a x-ray image, a magnetic resonance imaging (MRI) scan, a computed tomography (CT) scan, and/or a positron emission tomography (PET) scan, among others. The medical image 108 may be received from the medical image provider 112. The medical image provider 112 may include a medical imaging device/system that captures, manages, and/or presents the medical image 108 to a user 102. The user 102 may include a medical practitioner such as a doctor, a nurse, and/or a technician, a patient, and/or an administrator, among others. The user 102 may use the medical image 108 to diagnose an issue, a malignancy (cancer), and/or other illness associated with a patient.

The medical image 108 may include an object 110. The object 110 may include a biological structure of a patient. For example, the object 110 may include a malignant or a benign lesion. Alternatively, the object 110 may represent another structure associated with an organ and/or other body part of the patient.

Next, a computer assisted detection (CADe) module of the image analysis application 106 may partition the medical image into sub-regions. A size of the sub-regions may be determined by the CADe module based on a size of the object 110. For example, the object 110 that consumes a large portion of the medical image 108 may be partitioned to a large number of the sub-regions. Alternatively, the object 110 that consumes a small portion of the medical image 108 may be partitioned to a small number of the sub-regions. In yet another example scenario, the number of the sub-regions may be determined dynamically based on attributes associated with the medical image 108 such as dimensions, resolution, quality, and clarity.

The CADe module may process each sub-region to detect parts of the object 110. The parts of the object 110 may be detected in a selection of the sub-regions using a deep-learning neural network (DNN) model. The DNN model may include a machine learning mechanism based on learning data representations. Learning operations associated with the DNN model may vary from supervised learning to unsupervised learning.

In an example scenario, the CADe module may determine bounding boxes for the selection of the sub-regions (associated with the object 110). The bounding boxes may be evaluated based a confidence score detected as above a threshold. The confidence score (detected as above the threshold) may designate the parts of the object 110 as contained within the selection of the sub-regions. The confidence score may confirm that the CADe module has correctly recognized the parts of the object 110 within the bounding boxes representing the selection of the sub-regions (of the medical image 108). The threshold level may be determined automatically by the CADe based on positive and negative training models within the DNN model. Alternatively, the user 102 may manually determine the threshold level.

Next, a region of interest (ROI) 114 may be determined as a group comprising the selection of the sub-regions. The CADe module may determine the ROI 114 based on a comparison of similar orientations associated with the bounding boxes (representing the selection of the sub-regions) in relation to similar orientations of a positive training model of the DNN model. The similar orientations of the parts of the object 110 may describe orientation based relationships between the parts of the object 110 that are expected to match orientation based relationships within the positive training model. As such, the CADe module may conclusively detect the object 110 as a lesion when the attributes of the parts of the object 110 (such as the similar orientations) match comparable attributes in the positive training model.

In addition, the selection of the sub-regions may next be designated as the ROI 114 by the CADe module. Moreover, the medical image 108 may be provided with the ROI 114 to the user 102. The ROI 114 may alert the user 102 regarding a disease state (such as malignant/cancer or benign) associated with the object 110.

Previous example(s) to detect the object 110 in the medical image 108 are not provided in a limiting sense. Alternatively, the image analysis application 106 may perform operations associated with detecting the object 110 in the medical image 108 as a desktop application, a workstation application, and/or a server application, among others. The image analysis application 106 may also be a client interface of a server based application. Furthermore, the device 104 may include a component of the medical image provider 112. As such, the image analysis application 106 may include a service associated with the medical image provider 112.

The user 102 may interact with the image analysis application 106 with a keyboard based input, a mouse based input, a voice based input, a pen based input, and a gesture based input, among others. The gesture based input may include one or more touch based actions such as a touch action, a swipe action, and a combination of each, among others.

While the example system in FIG. 1 has been described with specific components including the device 104, the image analysis application 106, embodiments are not limited to these components or system configurations and can be implemented with other system configuration employing fewer or additional components.

Figure 2:
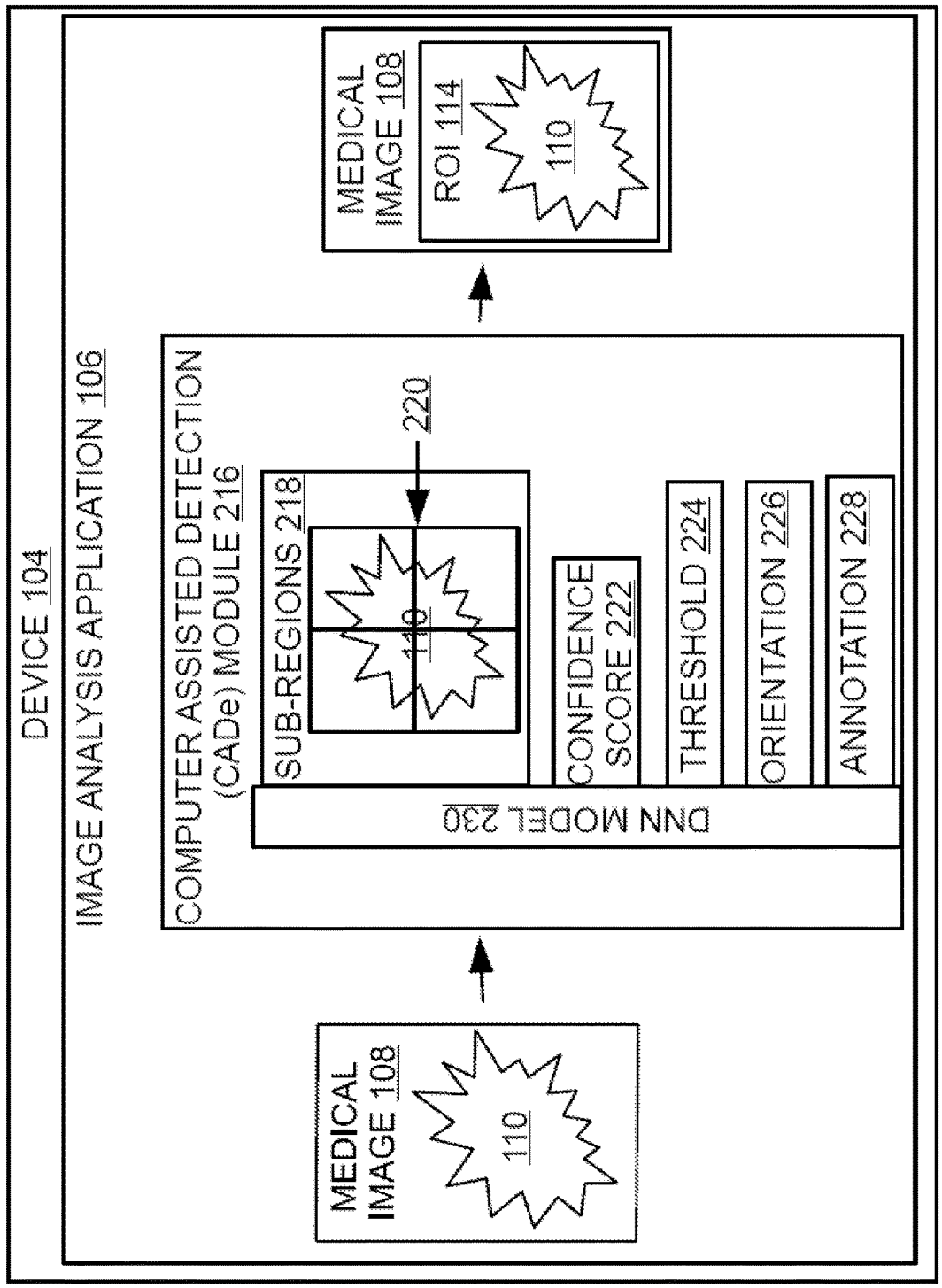
FIG. 2 shows a display diagram illustrating components of an image analysis application determining a region of interest (ROI) in the medical image and labelling the ROI with annotation(s), according to an embodiment of the invention.

FIG. 2 shows a display diagram illustrating components of the image analysis application 106 determining the ROI 114 in the medical image 108 and labelling the ROI 114 with annotation(s) 228. In an example scenario, the medical image 108 may be received as an input by the image analysis application 106. The CADe module 216 may partition the medical image 108 into sub-regions 218 and process the sub-regions 218 with a DNN model 230 to detect parts of the object 110. A selection 220 of the sub-regions 218 may be correlated to the parts of the object 110.

Bounding boxes may next be determined for the selection 220. The bounding boxes may be representations of the selection 220 and may be used interchangeable to refer to the selection 220. The bounding boxes may be evaluated based on a confidence score 222 detected as above a threshold 224 level. The confidence score 222 (detected as above the threshold 224 level) may designate the parts of the object 110 as contained within the selection 220 (of the sub-regions 218). As such, the confidence score 222 associated with the selection 220 (and/or the bounding boxes) may confirm that the CADe module 216 correctly identified and captured the parts of the object 110 within the selection 220.

Next, the ROI 114 may be determined as a group (of the sub-regions 218) that includes the selection 220. Similar orientations 226 associated with the bounding boxes may be comparable to similar orientations of a positive training model of the DNN model 230. The similar orientations 226 of the parts of the object 110 may describe orientation based relationships between the parts of the object 110 that are expected to match orientation based relationships within the positive training model. As such, the CADe module 216 may conclusively detect the object 110 as a lesion when the attributes of the parts of the object 110 (such as the similar orientations 226) match comparable attributes in the positive training model.

Similar orientations (226) of the bounding boxes may include similar and/or complimentary angular orientations between parts of the object 110. For example, parts of the object 110 within a sub-region 218 positioned in a right top quadrant may include edges that are oriented outwards toward a top and right directions. Similarly, other parts of the object 110 within the sub-regions 218 located in top left, bottom left, and bottom right quadrants of the selection 220 may include edges that are oriented outwards toward top left, bottom left, and bottom right directions, respectively.

Furthermore, similar orientations 226 may include similar distances between the parts of the object 110. In addition, the CADe module 216 may apply a non-maximum suppression (NMS) mechanism to the selection 220 of the sub-regions 218 to obtain the bounding boxes (associated with the selection 220) in relation to the object 110. Moreover, the DNN model 230 associated with a detection of the parts of the object 110 may include a region based convolutional neural network (R-CNN) model, a fast R-CNN model, a faster R-CNN model, a you only look once (YOLO) model, and/or a single shot multi-box (SSD) model, among others.

Furthermore, the CADe module 216 may label the selection 220 of the sub-regions within the ROI 114 with annotation(s) 228 associated with a type of tissue (in relation to the object 110). The type of tissue may include lobulated, spiculated, angular, clear boundary, oval, circumscribed, and/or abrupt interface, among others. The annotation(s) 228 may also include a relative position associated with a part (of the object 110). The relative position may include top, bottom, left side, right side, and/or combinations of relative positions, among others.

The CADe module 216 may emphasize the object 110 with the ROI 114 as a lesion within the medical image 108 by processing the medical image 108 with the DNN model 230. Furthermore, a training mechanism associated with the DNN model 230 may include a compensation for an unbalanced training data such as a majority of training medical images with no lesion and a minority of training medical images with a lesion. In addition, the training mechanism may include a down-sampling of the majority, an up-sampling of the minority, or a utilization of a cost sensitive mechanism, a gradient boost machine, or a hard negative mining mechanism.

Figure 3:
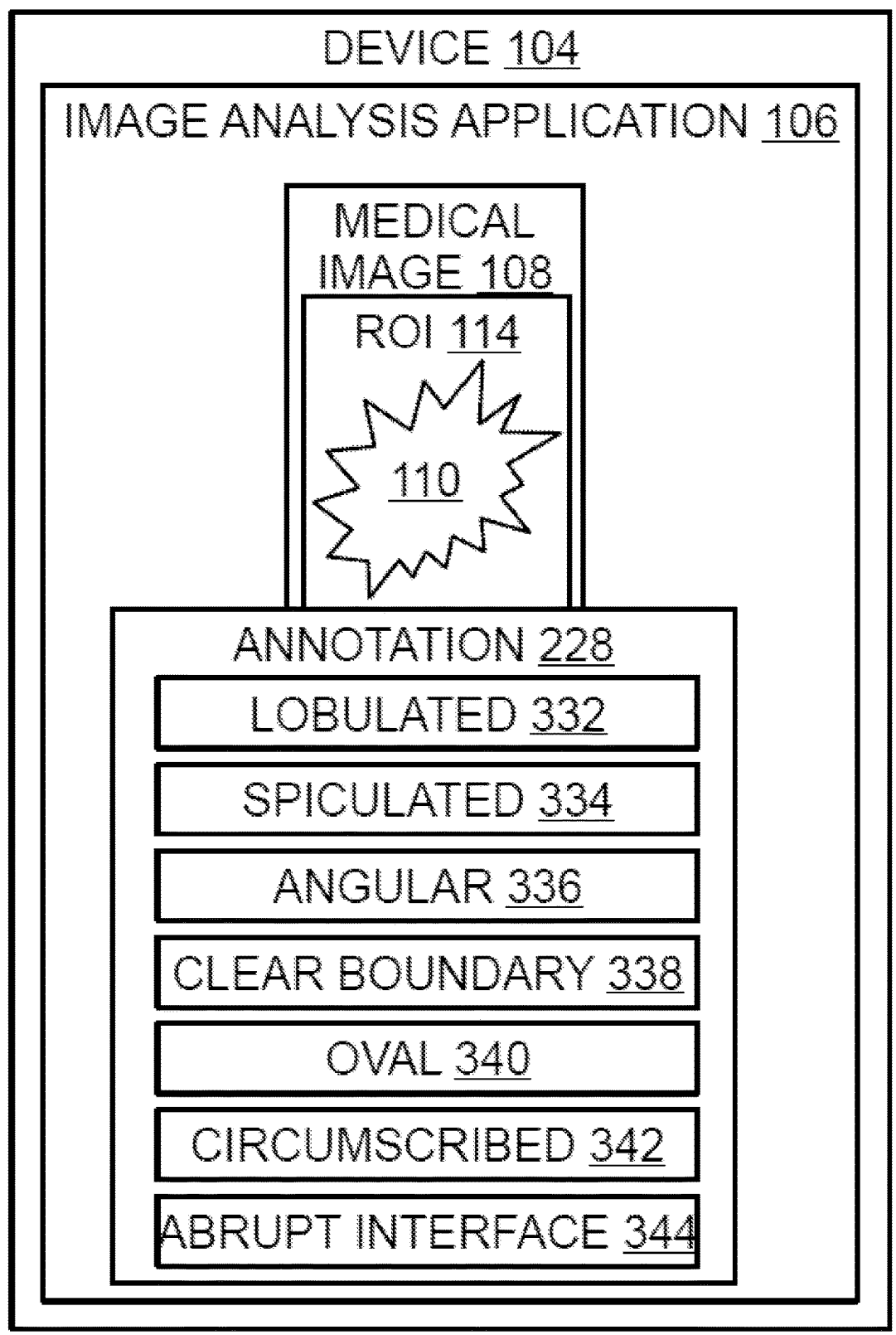
FIG. 3 shows another display diagram illustrating components of user interface allowing a user to interact with a ROI and annotation(s) associated with the ROI within a medical image, according to an embodiment of the invention.

FIG. 3 shows another display diagram illustrating components of a user interface allowing a user to interact with the ROI 114 and the annotation(s) 228 associated with the ROI 114 within the medical image 108. The image analysis application 106 (executed by the device 104) may provide the medical image 108 (or a digital copy) with the annotation(s) 228 and the ROI 114 to a user (such as a medical practitioner or a patient). Examples of the annotation(s) 228 may include a lobulated 332 sub-region, a spiculated 334 sub-region, an angular 336 sub-region, a clear boundary 338 sub-region, an oval 340 sub-region, a circumscribed 342 sub-region, and/or an abrupt interface 344 sub-region, among others.

The user interface may also be configured to allow the user to change the annotation(s) 228 associated with the ROI 114. In an example scenario, the image analysis application 106 may detect the user provide a change to the annotation(s) 228 to personalize the annotation(s) for the user. In response, the image analysis application 106 may identify a rate of concordance of the user in relation to the DNN model 230. The rate of concordance may include an evaluation of a correctness of the user when diagnosing medical images in relation to the object(s) within the medical images (whether malignant or benign).

The image analysis application 106 may determine the concordance rate of the user as above (or equal to) a threshold. The threshold may include a level which is correlated with a competence (associated with the user) when diagnosing an object within medical images as malignant or benign. In response to the determination associated with the concordance rate, the image analysis application 106 may retrain the DNN model 230 based on the change to the annotation(s) 228. The selection 220 (of the sub-regions 218) may be re-processed based on the change to the annotation(s) 228. Furthermore, the selection 220 of the sub-regions 218 may be re-labelled based on the change to the annotation(s) 228 to personalize the annotation(s) 228 to preference(s) of the user.

In another example scenario, the image analysis application 106 may determine the concordance rate of the user as below a threshold. In response, the change to the annotation(s) 228 (introduced by the user) may be rejected. A notification may be provided to the user to re-evaluate the change to the annotation(s). The notification may alert the user that the user may be incorrect regarding the change to the annotation(s) 228.

In yet another example scenario, the user may be allowed to interact, through an augmented reality display, with the medical image 108, the ROI 114, the annotation(s) 228. The annotation(s) 228 may also be provided as text, sound, or texture associated with the ROI 114.

The example scenarios and schemas in FIGS. 1 through 3 are shown with specific components, data types, and configurations. Embodiments are not limited to systems according to these example configurations. A device to detect an object in a medical image may be implemented in configurations employing fewer or additional components in applications and user interfaces. Furthermore, the example schema and components shown in FIGS. 1 through 3 and their subcomponents may be implemented in a similar manner with other values using the principles described herein.

Figure 4:
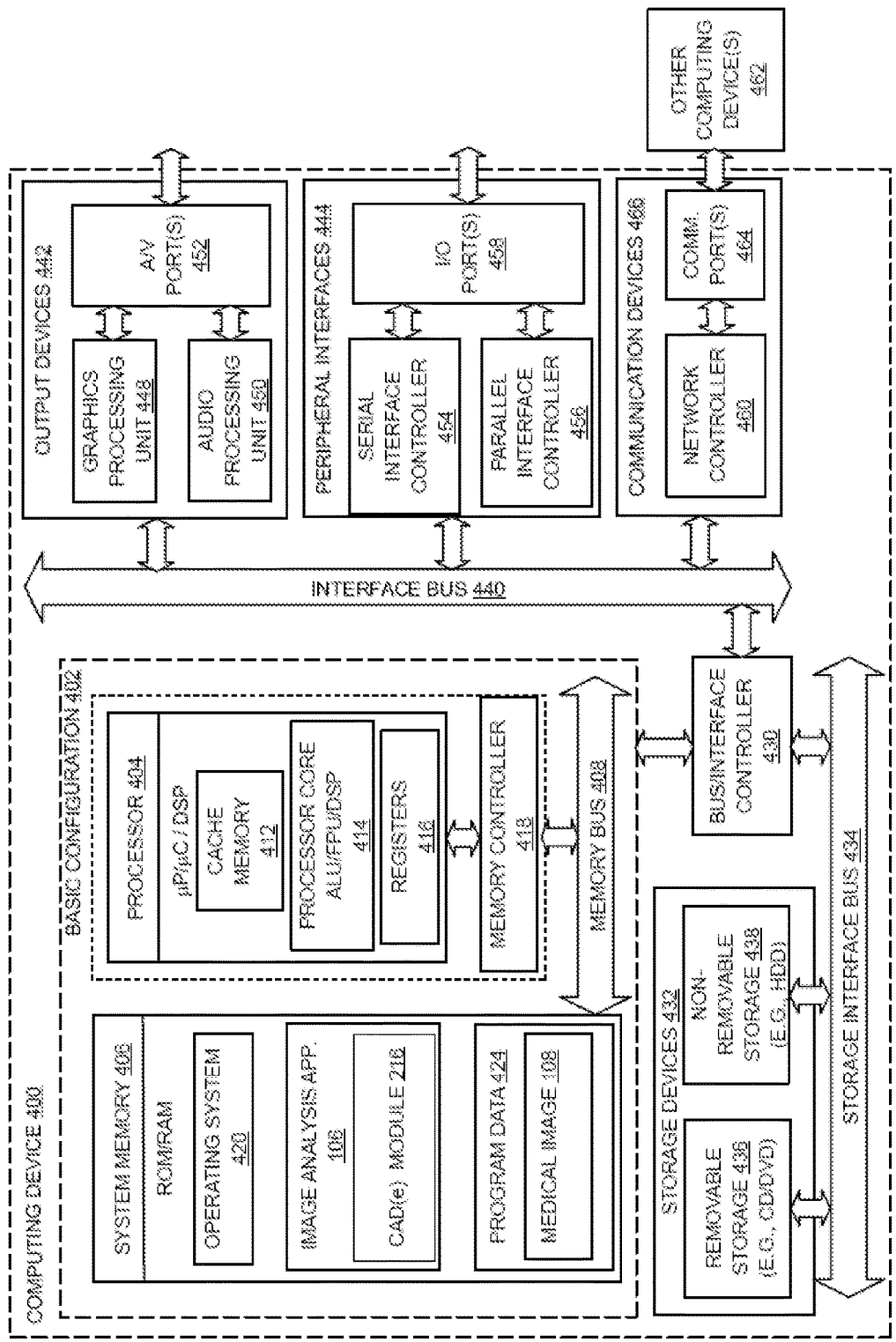
FIG. 4 is a block diagram of an example computing device, which may be used to detect an object in a medical image.

FIG. 4 is a block diagram of an example computing device, which may be used to detect an object in a medical image, according to embodiments.

For example, computing device 400 may be used as a server, desktop computer, portable computer, smart phone, special purpose computer, or similar device. In a basic configuration 402, the computing device 400 may include one or more processors 404 and a system memory 406. A memory bus 408 may be used for communication between the processor 404 and the system memory 406. The basic configuration 402 may be illustrated in FIG. 4 by those components within the inner dashed line.

Depending on the desired configuration, the processor 404 may be of any type, including but not limited to a microprocessor (µP), a microcontroller (µC), a digital signal processor (DSP), or any combination thereof. The processor 404 may include one more levels of caching, such as a level cache memory 412, one or more processor cores 414, and registers 416. The example processor cores 414 may (each) include an arithmetic logic unit (ALU), a floating-point unit (FPU), a digital signal processing core (DSP Core), a graphics processing unit (GPU), or any combination thereof. An example memory controller 418 may also be used with the processor 404, or in some implementations, the memory controller 418 may be an internal part of the processor 404.

Depending on the desired configuration, the system memory 406 may be of any type including but not limited to volatile memory (such as RAM), non-volatile memory (such as ROM, flash memory, etc.), or any combination thereof. The system memory 406 may include an operating system 420, the image analysis application 106, and a program data 424. The image analysis application 106 may include components such as the CADe module 216. The CADe module 216 may execute the instructions and processes associated with the image analysis application 106. In an example scenario, the CADe module 216 may receive the medical image as an input. The medical image may next be partitioned to sub-regions. Parts of the object may be detected in a selection of the sub-regions using a deep-learning neural network (DNN) model. Bounding boxes for the selection may also be determined. The bounding boxes may be evaluated based on a confidence score detected as above a threshold level. The confidence score may designate the parts as contained within the selection. Next, a region of interest (ROI) may be determined as a group including the selection. Similar orientations associated with the bounding boxes may be comparable to similar orientations of a positive training model of the DNN model. Furthermore, the selection may be designated as the ROI within the medical image. The medical image may also be provided with the ROI to a user.

Input to and output out of the image analysis application 106 may be captured and displayed through a display component that may be integrated to the computing device 400. The display component may include a display screen, and/or a display monitor, among others that may capture an input through a touch/gesture based component such as a digitizer. The program data 424 may also include, among other data, the medical image 108, or the like, as described herein. The object 110 in the medical image 108 may be identified and emphasized with the ROI 114 and annotation(s) 228, among other things.

The computing device 400 may have additional features or functionality, and additional interfaces to facilitate communications between the basic configuration 402 and any desired devices and interfaces. For example, a bus/interface controller 430 may be used to facilitate communications between the basic configuration 402 and one or more data storage devices 432 via a storage interface bus 434. The data storage devices 432 may be one or more removable storage devices 436, one or more non-removable storage devices 438, or a combination thereof. Examples of the removable storage and the non-removable storage devices may include magnetic disk devices, such as flexible disk drives and hard-disk drives (HDDs), optical disk drives such as compact disk (CD) drives or digital versatile disk (DVD) drives, solid state drives (SSDs), and tape drives, to name a few. Example computer storage media may include volatile and nonvolatile, removable, and non-removable media implemented in any method or technology for storage of information, such as computer-readable instructions, data structures, program modules, or other data.

The system memory 406, the removable storage devices 436 and the non-removable storage devices 438 are examples of computer storage media. Computer storage media includes, but is not limited to, RAM, ROM, EEPROM, flash memory or other memory technology, CD-ROM, digital versatile disks (DVDs), solid state drives, or other optical storage, magnetic cassettes, magnetic tape, magnetic disk storage or other magnetic storage devices, or any other medium which may be used to store the desired information and which may be accessed by the computing device 400. Any such computer storage media may be part of the computing device 400.

The computing device 400 may also include an interface bus 440 for facilitating communication from various interface devices (for example, one or more output devices 442, one or more peripheral interfaces 444, and one or more communication devices 466) to the basic configuration 402 via the bus/interface controller 430. Some of the example output devices 442 include a graphics processing unit 448 and an audio processing unit 450, which may be configured to communicate to various external devices such as a display or speakers via one or more A/V ports 452. One or more example peripheral interfaces 444 may include a serial interface controller 454 or a parallel interface controller 456, which may be configured to communicate with external devices such as input devices (for example, keyboard, mouse, pen, voice input device, touch input device, etc.) or other peripheral devices (for example, printer, scanner, etc.)

via one or more I/O ports 458. An example of the communication device(s) 466 includes a network controller 460, which may be arranged to facilitate communications with one or more other computing devices 462 over a network communication link via one or more communication ports 464. The one or more other computing devices 462 may include servers, computing devices, and comparable devices.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 400 may be implemented as a part of a specialized server, mainframe, or similar computer, which includes any of the above functions. The computing device 400 may also be implemented as a personal computer including both laptop computer and non-laptop computer configurations. Additionally, the computing device 400 may include specialized hardware such as an application-specific integrated circuit (ASIC), a field programmable gate array (FPGA), a programmable logic device (PLD), and/or a free form logic on an integrated circuit (IC), among others.

Example embodiments may also include methods to detect an object in a medical image. These methods can be implemented in any number of ways, including the structures described herein. One such way may be by machine operations, of devices of the type described in the present disclosure. Another optional way may be for one or more of the individual operations of the methods to be performed in conjunction with one or more human operators performing some of the operations while other operations may be performed by machines. These human operators need not be collocated with each other, but each can be only with a machine that performs a portion of the program. In other embodiments, the human interaction can be automated such as by pre-selected criteria that may be machine automated.

Figure 5:
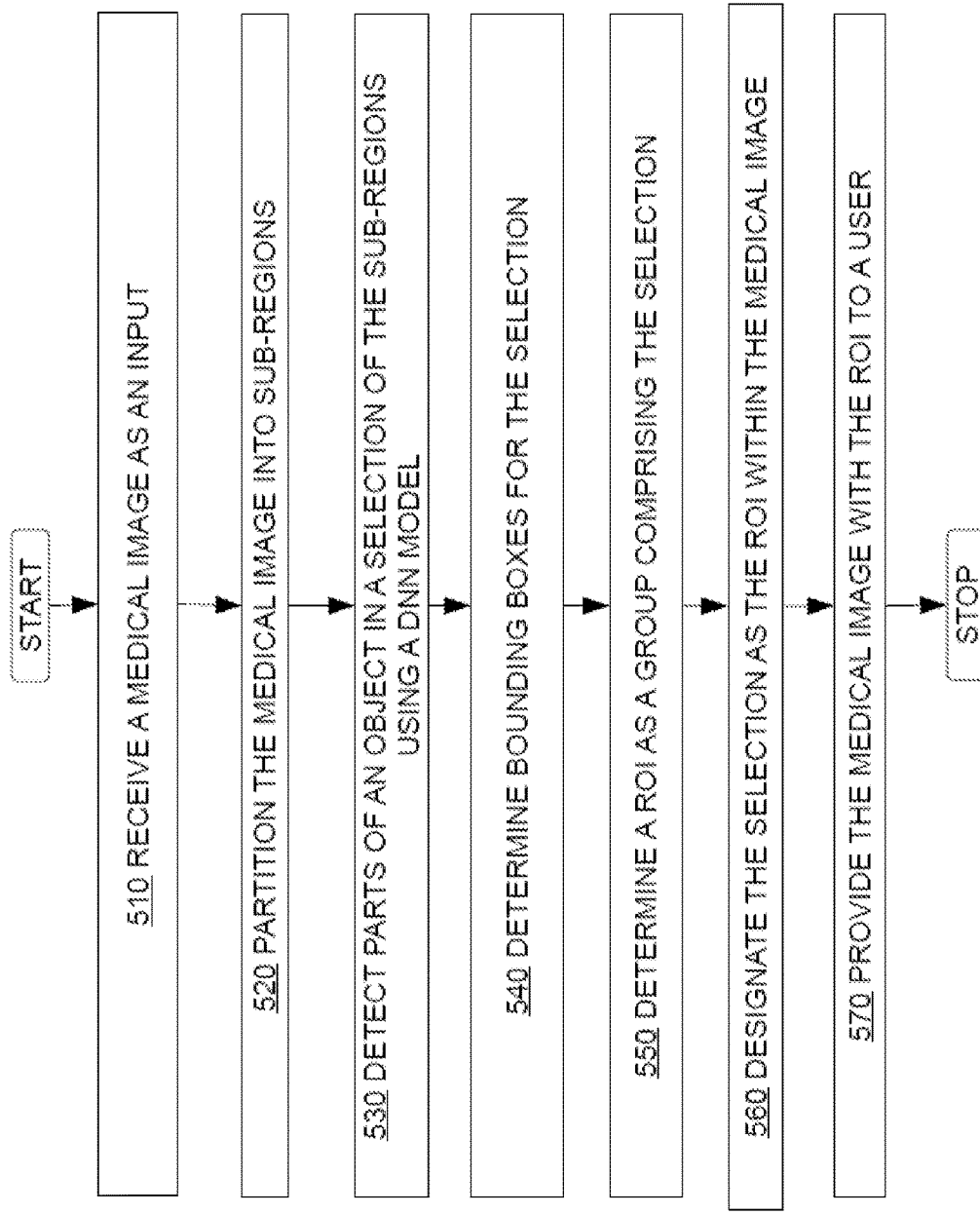
FIG. 5 is a logic flow diagram illustrating a process for detecting an object in a medical image, according to an embodiment of the invention.

FIG. 5 is a logic flow diagram illustrating a process for detecting an object in a medical image. Process 500 may be implemented on a computing device, such as the computing device 400 or another system.

Process 500 begins with operation 510, where an image analysis application may receive the medical image as an input. At operation 520, the medical image may be partitioned to sub-regions. At operation 530, parts of the object may be detected in a selection of the sub-regions using a deep-learning neural network (DNN) model. At operation 540, bounding boxes for the selection may be determined. The bounding boxes may be evaluated based on a confidence score detected as above a threshold level. The confidence score may designate the parts as contained within the selection.

Next, at operation 550, a ROI may be determined as a group including the selection. Similar orientations associated with the bounding boxes may be comparable to similar orientations of a positive training model of the DNN model. Furthermore, at operation 560, the selection may be designated as the ROI within the medical image. At operation 570, the medical image may be provided with the ROI to a user.

The operations included in process 500 is for illustration purposes. Detecting an object in a medical image may be implemented by similar processes with fewer or additional steps, as well as in different order of operations using the principles described herein. The operations described herein may be executed by one or more processors operated on one or more computing devices, one or more processor cores, specialized processing devices, and/or special purpose processors, among other examples.

A method of detecting an object in a medical image is also described. The method includes receiving the medical image as an input. The medical image may next be partitioned to sub-regions. Parts of the object may be detected in a selection of the sub-regions using a deep-learning neural network (DNN) model. Bounding boxes for the selection may also be determined. The bounding boxes may be evaluated based on a confidence score detected as above a threshold level. The confidence score may designate the parts as contained within the selection. Next, a region of interest (ROI) may be determined as a group including the selection. Similar orientations associated with the bounding boxes may be comparable to similar orientations of a positive training model of the DNN model. Furthermore, the selection may be designated as the ROI within the medical image. The medical image may also be provided with the ROI to a user.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:
1. A computer-based method comprising:
receiving, by a processor, a visual input;
utilizing, by the processor, a deep-learning neural network (DNN) to associate at least one bounding box of a plurality of bounding boxes with each unidentified object part of a plurality of unidentified object parts presented in the visual input;
   wherein the deep-learning neural network (DNN) comprises trained parameters based on model object parts of a plurality of model objects;
determining, by the processor, a plurality of orientation-based relationships between the plurality of unidentified object parts based on orientations between the plurality of bounding boxes;
determining, by the processor, a plurality of matching model object parts of a model object matching the plurality of unidentified object parts based on a similarity between:
   i) at least one orientation-based relationship of the plurality of orientation-based relationships, and
   ii) at least one model orientation-based relationship of a plurality of model orientation-based relationships;

identifying, by the processor, an object in the visual input based on the plurality of matching model object parts of the model object; and generating, by the processor, a digital representation of a region of interest (ROI) in the visual input, wherein the digital representation identifies the object.

2. The method of claim 1, wherein the at least one orientation-based relationship is based on angular orientations between the plurality of object parts.

3. The method of claim 1, wherein the determining the plurality of matching model object parts is further based on similar distances between the plurality of object parts.

4. The method of claim 1, further comprising:
applying a non-maximum suppression (NMS) to the visual input to determine the plurality of bounding boxes.

5. The method of claim 1, wherein, for the association of the at least one bounding box of the plurality of bounding boxes with each object part of the plurality of object parts, the DNN model is one of:
a region based convolutional neural network (R-CNN) model,
a fast R-CNN model, a faster R-CNN model,
a you only look once (YOLO) model, or
a single shot multi-box (SSD) model.

6. The method of claim 1, further comprising:
generating, by the processor, within the visual medical input, at least one annotation associated with a sub-region within the ROI.

7. The method of claim 6, wherein the visual input is a medical visual input and the object is a medical object.

8. The method of claim 7, wherein, the at least one annotation identifies a type of a tissue, and wherein the sub-region within the digital representation of the ROI comprises:
a digital representation of a lobulated interface,
a digital representation of a spiculated interface,
a digital representation of an angular interface,
a digital representation of a clear boundary interface,
a digital representation of an oval interface,
a digital representation of a circumscribed interface, or
a digital representation of an abrupt interface.

9. The method of claim 6, wherein the at least one annotation identifies a relative position associated with a matching object part of the plurality of matching object parts.

10. The method of claim 9, wherein the relative position is one of:
a top position,
a bottom position,
a left side position, or
a right side position.

11. The method of claim 6, further comprising:
causing, by the processor, to generate a user interface on a computing device displaying the digital representation of the ROI; and
wherein the user interface is configured to allow to make at least one change in the at least one annotation.

12. The method of claim 11, further comprising:
detecting, by the processor, the at least one change to personalize the at least one annotation based on the at least one change; and
identifying, by the processor, a rate of concordance between the at least one change and the DNN model.

13. The method of claim 12, further comprising:
determining, by the processor, that the concordance rate is above a threshold;
re-training, by the processor, the DNN model based on the at least one change to form the re-trained DNN model;
re-generating, by the processor, the digital representation of the ROI based on the re-trained DNN model; and
personalizing, by the processor, the at least one annotation based on the re-trained DNN model.

14. The method of claim 12, further comprising:
determining, by the processor, that the concordance rate is below a threshold;
rejecting, by the processor, the at least one change to the one or more annotations; and
generating, by the processor, via the user interface, a notification to re-evaluate the at least one change.

15. The method of claim 7, wherein the digital representation of ROI comprises a digital representation of a lesion.

16. The method of claim 7, further comprising:
training, by the processor, the DNN model based on an unbalanced training data in the medical visual input;
wherein the unbalanced training data comprises:
a majority of training medical images with no lesion and
a minority of training medical images with a lesion; and
wherein the training comprises at least one of:
down-sampling of the majority,
up-sampling of the minority,
utilizing a cost sensitive mechanism,
utilizing a gradient boost machine, or
utilizing a hard negative mining mechanism.

17. A system comprising:
a computing device;
a non-transitory computer readable medium associated with the computing device and having software instructions that, when executed by the computing device, cause the computing device to at least:
receive a visual input;
utilize a deep-learning neural network (DNN) to associate at least one bounding box of a plurality of bounding boxes with each unidentified object part of a plurality of unidentified object parts presented in the visual input;
wherein the deep-learning neural network (DNN) comprises trained parameters based on model object parts of a plurality of model objects;
determine a plurality of orientation-based relationships between the plurality of unidentified object parts based on orientations between the plurality of bounding boxes;
determine a plurality of matching model object parts of a model object matching the plurality of unidentified object parts based on a similarity between:
i) at least one orientation-based relationship of the plurality of orientation-based relationships, and
ii) at least one model orientation-based relationship of a plurality of model orientation-based relationships;
identify an object in the visual input based on the plurality of matching model object parts of the model object; and
generate a digital representation of a region of interest (ROI) in the visual input, wherein the digital representation identifies the object.

18. The system of claim 17, wherein the visual input is a medical visual input and the object is a medical object.

19. A non-transitory computer readable medium, comprising:
 software instructions that, when executed by a processor, cause a processor to at least:
  receive a visual input;
  utilize a deep-learning neural network (DNN) to associate at least one bounding box of a plurality of bounding boxes with each unidentified object part of a plurality of unidentified object parts presented in the visual input;
   wherein the deep-learning neural network (DNN) comprises trained parameters based on model object parts of a plurality of model objects;
  determine a plurality of orientation-based relationships between the plurality of unidentified object parts based on orientations between the plurality of bounding boxes;
  determine a plurality of matching model object parts of a model object matching the plurality of unidentified object parts based on a similarity between:
   i) at least one orientation-based relationship of the plurality of orientation-based relationships, and
   ii) at least one model orientation-based relationship of a plurality of model orientation-based relationships;
  identify an object in the visual input based on the plurality of matching model object parts of the model object; and
  generate a digital representation of a region of interest (ROI) in the visual input, wherein the digital representation identifies the object.

20. The non-transitory computer readable medium of claim 19, wherein the visual input is a medical visual input and the object is a medical object.

* * * * *